(12) United States Patent
Mathis

(10) Patent No.: US 7,758,639 B2
(45) Date of Patent: Jul. 20, 2010

(54) MITRAL VALVE DEVICE USING CONDITIONED SHAPE MEMORY ALLOY

(75) Inventor: Mark L. Mathis, Kirkland, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 554 days.

(21) Appl. No.: 11/655,710

(22) Filed: Jan. 18, 2007

(65) Prior Publication Data

US 2007/0135912 A1 Jun. 14, 2007

Related U.S. Application Data

(63) Continuation of application No. 10/359,016, filed on Feb. 3, 2003, now Pat. No. 7,314,485.

(51) Int. Cl.
*A61F 2/24* (2006.01)
(52) U.S. Cl. ............... 623/2.37; 623/2.36
(58) Field of Classification Search ........ 623/2.36–2.42
See application file for complete search history.

(56) References Cited

U.S. PATENT DOCUMENTS

| | | | |
|---|---|---|---|
| 3,974,526 A | 8/1976 | Dardik et al. | |
| 3,995,623 A | 12/1976 | Blake et al. | |
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,099,838 A | 3/1992 | Bardy | |
| 5,104,404 A | 4/1992 | Wolff | |

(Continued)

FOREIGN PATENT DOCUMENTS

EP 0893133 1/1999

(Continued)

OTHER PUBLICATIONS

Mathis, et al; U.S. Appl. No. 11/279,352, entitled "Mitral Valve Annuloplasty Device with Vena Cava Anchor," filed Apr. 11, 2006 (SLG # 10057-739.201).
Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

(Continued)

*Primary Examiner*—Suzette J Gherbi
(74) *Attorney, Agent, or Firm*—Shay Glenn LLP

(57) ABSTRACT

A mitral valve annulus reshaping device includes at least a portion that is formed of a biocompatible shape memory alloy SMA having a characteristic temperature, $A_f$, that is preferably below body temperature. The device is constrained in an unstable martensite (UM) state while being introduced through a catheter that passes through the venous system and into the coronary sinus of the heart. The reshaping device is deployed adjacent to the mitral valve annulus of the heart as it is forced from the catheter. When released from the constraint of the catheter, the SMA of the device at least partially converts from the UM state to an austenitic state and attempts to change to a programmed shape that exerts a force on the adjacent tissue and modifies the shape of the annulus. The strain of the SMA can be varied when the device is within the coronary sinus.

14 Claims, 9 Drawing Sheets

U.S. PATENT DOCUMENTS

| | | | |
|---|---|---|---|
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,662,703 A | 9/1997 | Yurek et al. |
| 5,676,671 A | 10/1997 | Inoue |
| 5,733,325 A | 3/1998 | Robinson et al. |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,503,271 B2 | 1/2003 | Duerig et al. |
| 6,537,314 B2 | 3/2003 | Langberg et al. |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,899,734 B2 | 5/2005 | Castro et al. |
| 6,908,478 B2 | 6/2005 | Alferness et al. |
| 6,935,404 B2 | 8/2005 | Duerig et al. |
| 6,949,122 B2 | 9/2005 | Adams et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 6,997,951 B2 * | 2/2006 | Solem et al. ............... 623/2.37 |
| 7,152,605 B2 | 12/2006 | Khairkhahan et al. |
| 7,175,653 B2 | 2/2007 | Gaber |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0040771 A1 | 2/2003 | Hyodoh et al. |

| Publication No. | Date | Inventor |
|---|---|---|
| 2003/0069636 A1 | 4/2003 | Solem et al. |
| 2003/0078465 A1* | 4/2003 | Pai et al. .................... 600/16 |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0130730 A1 | 7/2003 | Cohn et al. |
| 2003/0135267 A1 | 7/2003 | Solem et al. |
| 2003/0171776 A1 | 9/2003 | Adams et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0065598 A1 | 3/2005 | Mathis et al. |
| 2005/0080483 A1* | 4/2005 | Solem et al. ............... 623/2.11 |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1* | 6/2005 | Gordon et al. ............... 600/37 |
| 2005/0137685 A1* | 6/2005 | Nieminen et al. .......... 623/2.11 |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0191121 A1 | 8/2006 | Gordon |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |
| 2009/0228100 A1* | 9/2009 | Solem et al. ............... 623/2.37 |
| 2010/0030330 A1* | 2/2010 | Bobo et al. ................ 623/2.36 |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| WO | WO 98/56435 A1 | 12/1998 |
| WO | WO 00/44313 A1 | 8/2000 |
| WO | WO 00/60995 A2 | 10/2000 |
| WO | WO 00/74603 A1 | 12/2000 |
| WO | WO 01/00111 A1 | 1/2001 |
| WO | WO 01/19292 A1 | 3/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |

OTHER PUBLICATIONS

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. 1997; 96(6): 1893-1898.

Mathis et al., U.S. Appl. No. 11/782,490 entitled "Device and method for modifying the shape of a body organ," filed Jul. 24, 2007.

Mathis et al., U.S. Appl. No. 11/782,508, entitled "Device and method for modifying the shape of a body organ," filed Jul. 24, 2007.

Mathis et al., U.S. Appl. No. 11/782,527 entitled "Device and method for modifying the shape of a body organ," filed Jul. 24, 2007.

Mathis et al; U.S. Appl. No. 11/963,417 entitled "Device and method for modifying the shape of a body organ," filed Dec. 21, 2007.

Hayner et al.; U.S. Appl. No. 12/189,527 entitled "Catheter cutting tool," filed Aug. 11, 2008.

El-Maasarany et al.; The coronary sinus conduit function: Anatomical study (relationship to adjacent structures); http://europace.oxfordjournals.org/cge/content/full/7/5/475.

Mathis et al.; U.S. Appl. No. 12/016,054 entitled "Fixed anchor and pull mitral valve device and method," filed Jan. 17, 2008.

Gordon et al.; U.S. Appl. No. 11/971,174 entitled "Medical device delivery system," filed Jan. 8, 2008.

Nieminen et al; U.S. Appl. No. 12/060,781 entitled "Tissue shaping device," filed Apr. 1, 2008.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

* cited by examiner

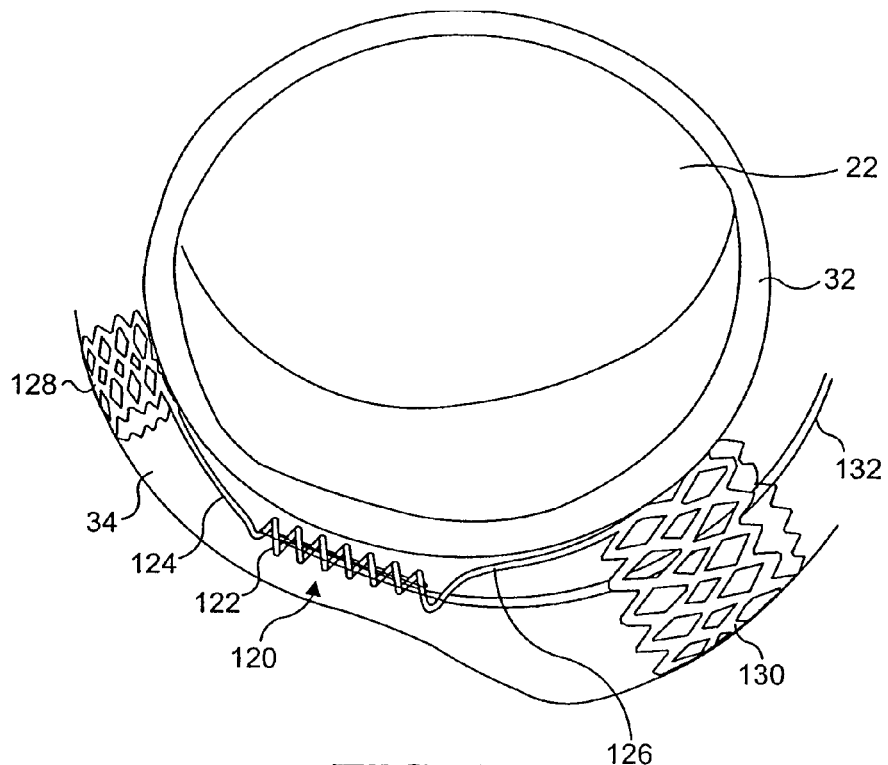
FIG. 15
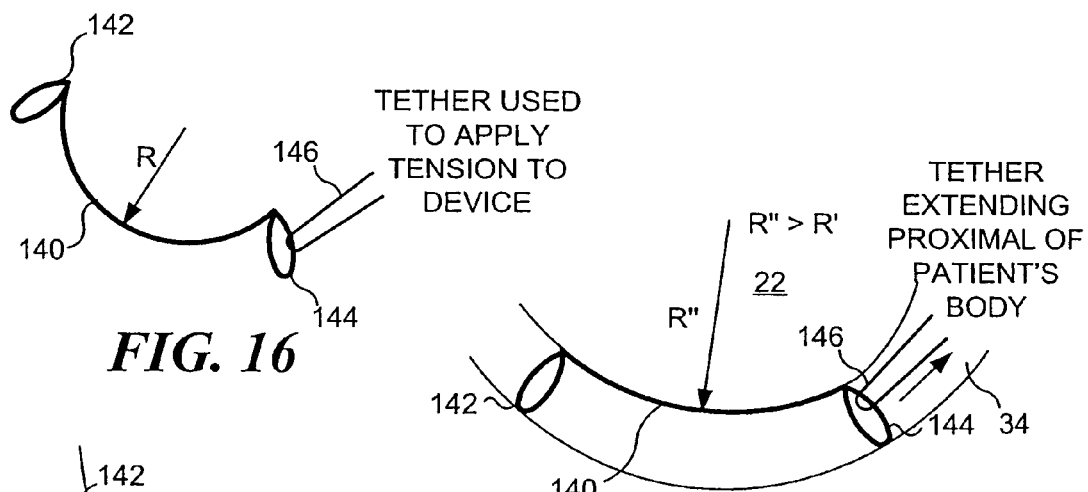
FIG. 16
FIG. 17
FIG. 18

MITRAL VALVE DEVICE USING CONDITIONED SHAPE MEMORY ALLOY

CROSS REFERENCE TO RELATED APPLICATIONS

This application is a continuation of pending U.S. application Ser. No. 10/359,016, filed Feb. 3, 2003, now U.S. Pat. No. 7,314,485 entitled "Mitral Valve Device Using Conditioned Shape Memory Alloy," which application is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference

FIELD OF THE INVENTION

The present invention generally pertains apparatus and a method for treating mitral insufficiency and, more specifically, for treating dilation of the mitral valve annulus of the human heart and concomitant blood leakage, by using force applied with a device formed at least in part of a shape memory alloy that is conditioned to a martensite state before being inserted into a venous system of a patient and advanced into the patient's coronary sinus.

BACKGROUND OF THE INVENTION

Mitral insufficiency is the inability of the mitral valve to close completely and can occur for several reasons, such as ischemic disease, degenerative disease of the mitral apparatus, rheumatic fever, endocarditis, congenital heart disease, and cardiomyopathy. Because the mitral valve does not close completely, "mitral regurgitation" occurs. Blood thus leaks back through the mitral valve, and the heart becomes less efficient. Over time, the reduced pumping efficiency can cause the heart to become enlarged.

The four major structural components of the mitral valve are the annulus, the two leaflets, the chorda, and the papillary muscles. Any one or all of these components, in different combinations, may be injured or suffer from a congenital defect and cause the insufficiency. Annular dilatation is a major component in the pathology of mitral insufficiency, regardless of its cause. Moreover, many patients experience mitral insufficiency primarily, or only, due to posterior annular dilatation. Annular dilation can occur when the annulus of the anterior leaflet does not dilate because it is anchored to the fibrous skeleton of the base of the heart.

Studies of the natural history of mitral insufficiency have determined that totally asymptomatic patients with severe mitral insufficiency usually progress to severe disability within five years. At present, the preferred treatment for this condition consists of either mitral valve replacement or repair; however, both types of treatment require open heart surgery. Replacement can be performed using either mechanical or biological valves.

Replacement of a mitral valve with a mechanical valve carries the risk of thromboembolism (due to formation of a clot) and requires that an anticoagulant be administered to the patient, with all its potential hazards, whereas a biological prostheses replacement may suffer from limited durability. Another hazard with replacement is the risk of endocarditis (inflammation of the endocardium). These risks and other related complications of valve replacement are greatly diminished if valve repair is carried out, rather than valve replacement.

Mitral valve repair is theoretically possible if a substantially normal anterior leaflet is present. The four basic techniques for repair include: (a) the use of an annuloplasty ring; (b) quadrangular segmental resection of a diseased posterior leaflet; (c) shortening of elongated chorda; and (d) transposition of posterior leaflet chorda to the anterior leaflet.

Annuloplasty rings are employed to achieve a durable reduction of the annular dilatation. Typically, annuloplasty rings are sutured along the posterior mitral leaflet adjacent to the mitral annulus in the left atrium. The installation procedure employed depends upon the specific annuloplasty ring being installed. For example, a Duran ring encircles the valve completely, whereas others types of rings are open towards the anterior leaflet. The ring can either be rigid, as in a Carpentier ring, or flexible, but non-elastic, like the Duran ring or a Cosgrove-Edwards ring.

Effective treatment of mitral insufficiency currently requires open-heart surgery, involving a total cardiopulmonary by-pass, aortic cross-clamping, and temporary cardiac arrest. For certain groups of patients, open-heart surgery and the associated procedures that must be performed are particularly hazardous. It is likely that elderly patients and patients with a poor left ventricular function, renal disease, severe calcification of the aorta, previous cardiac surgery, or other cardiovascular diseases, would particularly benefit from a less invasive approach, even if repair of the mitral valve is incomplete. The current trend towards less invasive coronary artery surgery, without cardiopulmonary by-pass, as well as percutaneous transluminal coronary angioplasty (PTCA) will also call for the development of a less invasive method for repair of the mitral insufficiency that is often associated with PTCA.

To perform typical open surgical procedures in ways that are less invasive will likely require use of technology for storing or transmitting energy so that apparatus for implementing the treatment can be delivered within a limited space, and positioned and released in remote locations in the body. Hydraulic conduits such as those used to inflate balloon catheters, and an electrical current have been employed to actuate devices remotely in the human body. However, one of the most reliable and effective remote actuation methods utilizes self actuating components formed of a shape memory alloy (SMA) that releases stored strain energy at a desired location within the body of a patient.

Materials capable of shape memory are well known. A structural element made of such materials can be deformed from an original, heat-stable configuration to a second, heat-unstable configuration. In the heat-unstable configuration, the element is said to have shape memory because, upon the application of heat alone, the element can be caused to revert, or to attempt to revert, from its deformed configuration to its original, heat-stable configuration. The metal element "remembers" its programmed shape. Programming is accomplished by thermally or mechanically stressing the element, while bending it into a desired shape.

Among certain metallic alloys, the shape memory capability occurs when the alloys undergo a reversible transformation from an austenitic state to a martensite state, with a change in temperature. This transformation is sometimes referred to as a thermo-elastic martensite transformation. An element made from such alloys, for example a hollow sleeve, is easily loaded and deformed from its original configuration to a new configuration if it has been cooled below the temperature at which the alloy is transformed from the austenitic state to the martensite state. The temperature at which this transformation from austenite to martensite begins is usually referred to as $M_s$ (martensite start), and the temperature at which the transformation is complete is $M_f$ (martensite final). When an element that has been thus deformed is warmed to the temperature at which the alloy starts to recover back to an austenite phase, referred to as $A_s$, the deformed object will begin to recover to its programmed shape. Assuming that the element is unconstrained, it will assume its programmed shape when it has been fully transformed to an austenitic state (where $A_f$ is the temperature at which the recovery is complete).

Many shape memory alloys (SMAs) are known to display stress-induced martensite (SIM) characteristics. When an SMA element exhibiting SIM is stressed at a temperature above $M_s$ (so that the austenitic state is initially stable), but below $M_d$ (the maximum temperature at which martensite formation can occur even under stress), it first deforms elastically and then, at a critical stress, begins to transform to a martensite state.

Depending on whether the temperature is above or below $A_s$, the behavior of an SMA when the deforming stress is released differs. If the temperature is below $A_s$, the thermally induced martensite is stable; but if the temperature is above $A_s$, the martensite is unstable, so that the SMA transforms back to austenite and returns (or attempts to return) to its original shape. As used herein, the term "unstable martensite" or (UM) describes a martensite state of an SMA alloy that is at or above the alloy's $A_s$ temperature. Under certain circumstances, this effect is actually seen in almost all alloys that exhibit a thermo-elastic martensitic transformation, along with the shape memory effect. However, the extent of the temperature range over which UM is observed and the stress and strain ranges for the effect vary greatly with the alloy.

Various proposals have been made to employ shape memory alloys in the medical field. For example, U.S. Pat. No. 3,620,212 to Fannon et al. teaches the use of an SMA intrauterine contraceptive device; U.S. Pat. No. 3,786,806 to Johnson et al. teaches the use of an SMA bone plate; and U.S. Pat. No. 3,890,977 to Wilson teaches the use of an SMA element to bend a catheter or cannula.

These prior art medical SMA devices rely on the property of shape memory to achieve their desired effects, i.e., they rely on the fact that when an SMA element is cooled to its martensitic phase and is subsequently deformed, it will retain its new shape. But when the deformed SMA is warmed to its austenitic phase, the original shape will be recovered. Heating a medical SMA device to activate a recovery to a programmed shape within a patient's body is quite complicated and is generally not practical, because complex and sometimes unreliable heat energy sources are needed to cause the change in state of the metal. In many SMAs, there is a relatively large hysteresis as the alloy is transformed between its austenitic and martensitic states, so that thermal reversing of the state of an SMA element may require a temperature excursion of several tens of degrees Celsius. The use that can be made of SMA medical devices in the body of a human patient is limited because of these factors and because: (a) it is inconvenient to engage in any temperature manipulation of a device in-vivo; and, (b) human tissue cannot be heated or cooled beyond certain relatively narrow limits (approximately 0-60 degrees C. for short periods) without suffering temporary or permanent damage.

It would therefore be desirable to use the advantageous property of shape memory alloys, i.e., their ability to return to a programmed shape after experiencing a relatively substantial deformation, in mitral valve therapy, without requiring the delicacy of alloying control and/or the temperature control of placement or removal needed by thermally activated SMA devices.

Nickel titanium SMA compositions can be tuned with appropriate heat treatments to adjust the $A_f$ temperature of the material. Compositions comprising nickel, in about 50 to 60% Ni atomic percent (hereinafter referred to as at. %), using Ti for the remainder of the composition, can have characteristic $A_f$ temperatures ranging from 0-100° C. By heat-treating these alloys at or near approximately 500° C., it is possible to precipitate nickel in or out of the Ni—Ti matrix so as to adjust the $A_f$ to a specific and desired temperature.

The $A_f$ temperature of a SMA can be readily determined. By deforming a cooled SMA sample (comprising stable thermally induced martensite at a temperature well below its $A_f$) from its programmed shape and then increasing its temperature, a distinct temperature can be identified at which the sample has recovered fully to its programmed shape. It is at this $A_f$ temperature that the entire sample has transformed back to an austenite state. The $A_f$ temperature of local regions of a component can be adjusted individually and determined in a similar manner, also.

By adjusting the SMA's characteristic $A_f$ below body temperature, the alloy will exhibit super-elastic or pseudo-elastic properties at body temperature, allowing it to experience as much as 8% strain and still fully recover. In this application, the SMA is initially austenitic and, under no load, it is not strained. Upon loading the device, the strain developed in the SMA causes it to undergo a phase transformation to UM. Upon unloading, the SMA that is UM will recover to its programmed shape and revert back to an austenitic phase. During loading and unloading, SMA alloys are internally stressed and deliver resistance forces of different magnitudes at the same strain state. The loading curve describes loading (stress) versus strain required to deform an element from its programmed shape while the unloading curve is descriptive of the load (stress) versus strain curve exhibited while the element is recovering to its programmed shape after being loaded, and thus recovering to a zero strain state. The unloading curve can be much lower in magnitude than the loading curve. This bimodal (BM) elastic effect (i.e., the hysteresis between the two curves) can only be accomplished at a constant temperature if the material is conditioned to a state of UM (along the loading curve).

A device made from an SMA alloy can be manipulated from one performance level to another simply by varying the load applied to the device, thereby changing its level of stored strain energy. The bimodal (BM) effect between the curves enables a medical device to be assisted, using force, to a different equilibrium condition as the device bears on soft tissue. A medical device made from this family of SMAs can be deployed from a delivery system (allowing it to partially recover towards a programmed shape along its unloading curve) to achieve a balanced, low force condition in a patient's body. Using hydraulic, pneumatic, electrical, heat energy, or mechanical force, the device can be assisted to further displace tissue, by adjusting the load along the unloading curve, to approach a zero strain state. As the assisting force is removed, an elastic recoil of the tissue will displace the device in a reverse direction, towards a slightly more deformed shape, thus causing the alloy to resist bending more effectively by forcing it to the loading curve (i.e., to a stiffer condition). This bimodal (BM) effect acts as a one-way ratchet with minimal moving parts and thus enables effective and reliable adjustment of load bearing elements in the human body to achieve a desired effect on adjacent tissue.

UM can be stress induced in SMAs by imparting sufficient stress to transform an SMA element from an austenite to a UM state. This type of UM is referred to as strain induced. Also, SMA elements can be cooled to form stable, thermally induced martensite. The SMA element can then be easily deformed to a new shape, constrained in the new shape, and then warmed to a temperature above the $A_f$ temperature of the SMA to create a UM state. There are also combinations of these conditioning techniques that will accomplish the same UM condition. These conditioning methods inevitably create a condition of stored strain energy sufficient to enable self-actuation and adjustment of medical devices remotely placed in a patient's body.

An SMA element with an $A_f$ temperature adjusted above body temperature will remain in a state of stable martensite in the human body if unconstrained. At body temperature, an SMA element in this condition will not recover to an original programmed shape upon loading and unload. If sufficiently loaded, its shape will be altered and it will remain in the new shape. In this bending process, SMA comprising primarily nickel and titanium, as described above, work hardens at a high rate, which increases the alloy's effective stiffness and strength. A device that is self-actuating must avoid these problems if it is to be practical for use in modifying the annulus of a mitral valve to correct mitral valve leakage. Accordingly, such a device should be formed using an SMA that is super-elastic at body temperatures, so that when unloaded, the device will recover to its programmed shape when unloaded within the body of a patient.

SUMMARY OF THE INVENTION

The present invention takes advantage of the coronary sinus being adjacent to the mitral annulus, and the properties of SMAs that are conditioned to a state of UM. Using the present invention, mitral valve repair can be carried out using catheter-guided techniques to deploy a device within the coronary sinus, so that the device self actuates when released from a constraint.

According to the present invention, a device for treatment of mitral insufficiency is sized so as to be capable of insertion into the coronary sinus and is formed at least in part of an SMA having two states. In a first state, the device has a shape adaptable to fit the shape of the coronary sinus, but when allowed to transform to the second state, the device assumes a second shape that enables a force to be applied to modify the mitral valve annulus in a way that reduces mitral valve regurgitation. The transformation from the first shape to the second shape is facilitated at least partially by utilizing the release of strain energy as the device or a portion thereof is unconstrained and allowed to change from a state of UM to a lower strain condition. Thus, the device may change to an austenite state upon being unloaded. UM is generally induced at strain levels above about 1.0%, and more typically, at strain levels above about 1.5%.

As used herein, the term "coronary sinus" is meant to refer to not only the coronary sinus itself, but in addition, to encompass the venous system associated with the coronary sinus, including the great cardiac vein, the coronary sinus, the junction between the cardiac vein and the coronary sinus, and the right atrium of the human heart. The present invention is intended to be delivered into the coronary sinus, because the coronary sinus is advantageously located adjacent to the mitral valve of the human heart and in a location to which the device can be maneuvered through peripheral vasculature, using common or custom catheter-based instruments, without the need for an open chest operation.

According to another aspect of the present invention, a method of altering the shape of the mitral valve annulus includes the steps of inserting a device at least partially comprising an SMA constrained in a state of UM, into the coronary sinus, and releasing the constraint to allow the device to recover towards a previously programmed shape and lower strain state. In yet another aspect of the invention, a force is applied to the device while it is positioned in the coronary sinus so as to adjust the intrinsic stiffness and shape of the device and thereby alter the shape of the coronary sinus to modify the shape of the mitral valve annulus.

Preferably, the device is formed from an SMA that has been treated so that it is super-elastic within the body of a patient. The super-elastic properties are employed by the device in its change of configuration between constrained and relaxed states. An appropriate treatment can involve a combination of cold working (for example by swaging, drawing or, in particular, by mandrel expansion) and heat treatment at a temperature that is less than the recrystallization temperature of the alloy while the device is constrained in the configuration resulting from the cold work. A plurality of the cold work and heat treatment steps can be used. The device can then be deformed towards the configuration of its first shape in its constrained first state, the deformation being recoverable and substantially elastic. In this way, deformations of up to 8% strain can be imparted and recovered substantially elastically.

Alloys from which the device can be made include Ni—Ti based alloys, especially Ni—Ti binary alloys, such as those in which the nickel content is at least about 50% at. %, and preferably, at least about 50.5 at. %. The nickel content will usefully be less than about 54 at. %, and preferably, less than about 52 at. %. The device may be produced from other Ni—Ti based alloys, including alloys with ternary and quaternary additions. Examples of other elements that can be incorporated as additions to the alloy include Fe, Co, Cr, Al, Cu, and V. Other elements can be present in amounts up to about 10 at. %, and preferably, up to about 5 at. %.

In still another aspect of the present invention, a device is defined for treatment of mitral insufficiency. The device has an elongate body with dimensions selected so that the device can readily be inserted into the coronary sinus and at least in part is formed of a material having two states, including a first state in which the device has a shape that is adaptable to fit the shape of the coronary sinus, and a second state in which the device is transformed from the said first state to assume a shape having either a reduced radius of curvature or an increased radius of curvature. The radius of curvature of the coronary sinus is thus modified by the device, as well as the radius of the circumference of the mitral valve annulus, when the elongate body is positioned in or through the coronary sinus. The distal and proximal ends of the device, and points in between, apply localized forces on the mitral annulus at one or more discrete locations.

The transformation from the first to the second state is facilitated through the use of SMA constrained in a UM state, utilizing the release of strain energy as the device or portion thereof is unconstrained and allowed to transform from UM to a lower strain condition (and in at least one embodiment, to transform to stable austenite) upon unloading. The constraining element can be a typical catheter, e.g., of the type commonly used to deliver devices such as arterial stents.

An optimal method to use the above-described device includes deploying the device and then assisting it into a more optimal shape using a drawstring (tether) or other element, to vary the length of the device along one side and thereby cause a curvature enhancement of the device. This mechanical assistance will alter the stiffness and enhance performance of the device by utilizing the BM effect of UM, as described above.

In another embodiment, the device includes one or more stents that are formed of SMA alloy having UM properties for self-deployment and adjustment. In this embodiment, the device may further include wires and/or spring elements for shortening the distance between the stent sections using UM properties. The stent sections may be actuated by force provided by balloon devices or they may be self-actuated by the transformation from UM, as described above. Stent radial stiffness and wire tension performance is adjustable using mechanical or balloon devices to enable a new stiffness condition using the BM effect of UM. The devices could optionally include dedicated anchor structures that apply a low expansive force against the wall of the coronary sinus.

In one preferred embodiment, the present invention is directed to an assembly that includes a tubular delivery device in which the mitral annulus shaping device is disposed and constrained, prior to insertion into a patient's body through a catheter. The constraint imparts a strain in excess of 1.5% on a region of the mitral valve annulus reshaping device so that it is UM at normal body temperature.

Still another aspect of the present invention is directed to a construction in which a mitral annulus shaping device can be constrained in a strained configuration for delivery into the coronary sinus within a hollow member, such as a catheter. A suitable catheter might be formed, for example, from a polymeric material that constrains the mitral annulus shaping device while disposed in the catheter, and which facilitates discharge of the mitral valve annulus reshaping device from the catheter.

The mitral valve annulus reshaping device can be discharged from the delivery device either by advancing the mitral annulus shaping device forward with respect to the delivery device, or by withdrawing the delivery device from the site at which the mitral annulus shaping device is being deployed.

The configuration of the delivery device is selected so that it can properly contain the mitral valve annulus reshaping device and withstand the elastic forces exerted by the device prior to discharge from the delivery device. Preferably, the delivery device has a minimum wall thickness necessary to satisfy these criteria. A constraint provided according to the present invention has the advantage of being thin-walled and flexible in bending, while also having sufficient radial stiffness to be able to withstand the forces exerted by the mitral annulus shaping device as it attempts to recover, even when these forces are applied over a long period of time, at temperatures above body temperature.

Preferably, the mitral valve annulus reshaping assembly includes means for facilitating release of the mitral valve annulus reshaping device from within the delivery device. For example, one of the contacting surfaces of the shaping device and the delivery device can be coated with a material that reduces friction effects between those surfaces.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 15 illustrates the coronary sinus and mitral valve and shows a mitral valve annulus reshaping device comprising stent elements that are self-deploying from a state of unstable martensite to a second state with an SMA spring connector and bias stiffness adjusting tether in a human coronary sinus;

FIG. 16 is a schematic illustration showing a programmed shape of another mitral valve annulus reshaping device having a wire or arched leaf spring with a radius of curvature, R;

FIG. 17 is a schematic diagram illustrating the mitral valve annulus reshaping device of FIG. 16 disposed within the coronary sinus and partially straightened to have a larger radius of curvature, R'; and FIG. 18 is a schematic diagram illustrating the mitral valve annulus reshaping device of FIGS. 16 and 17, after the device has been tuned with a tether to have provide a different force against the mitral valve and to have an even larger radius of curvature, R".

DETAILED DESCRIPTION OF THE INVENTION

To understand the present invention, it is necessary to understand austenite to martensite transformations that occur in a SMA and understand how SMA can be used advantageously in the coronary sinus for modifying the mitral valve annulus. After discussing these concepts, the disclosure will turn to specific devices, methods and assemblies of the present invention.

Figure 1:
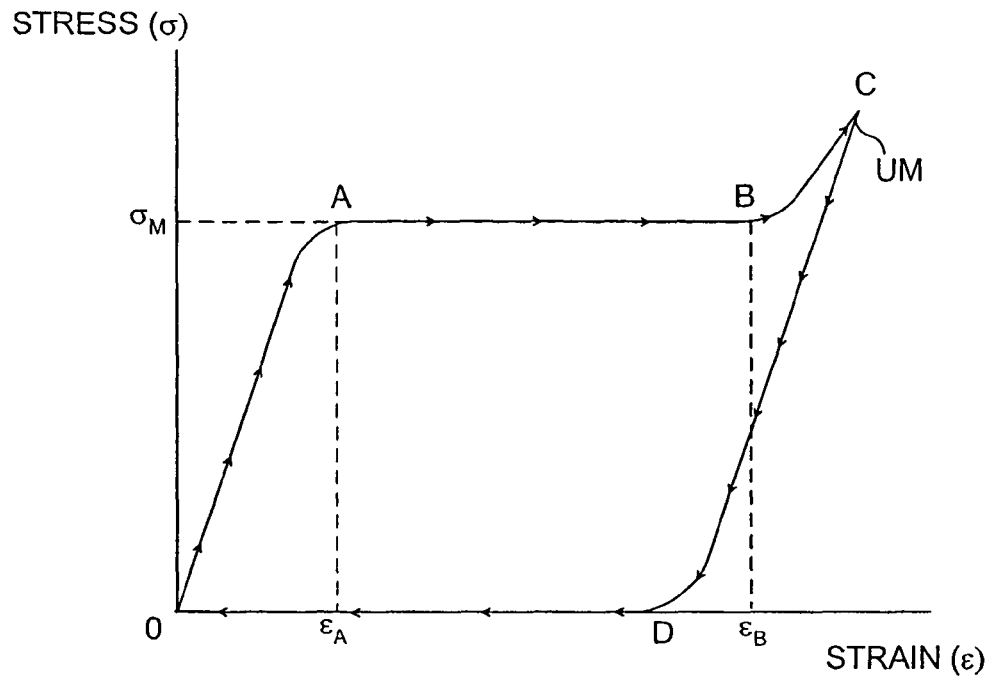
FIG. 1 illustrates the stress-strain behavior of an alloy, which exhibits stress versus strain behavior due to induced martensite when the $A_f$ temperature is at or above the temperature of a human body.
Figure 2:
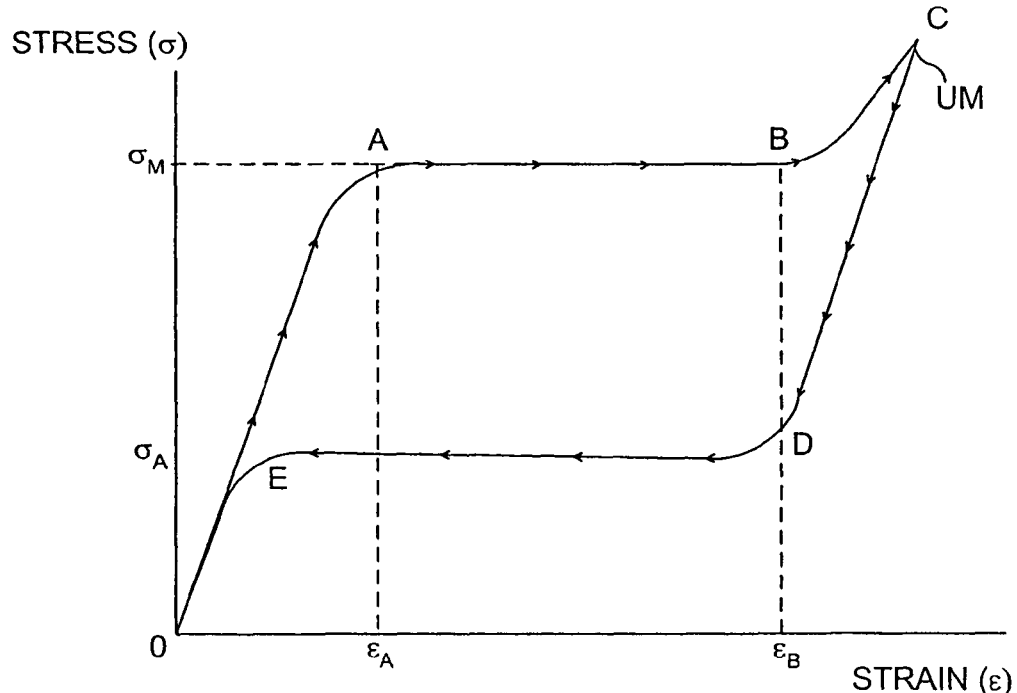
FIG. 2 illustrates the stress-strain behavior of an alloy, which exhibits constant stress versus strain behavior due to induced martensite when the $A_f$ temperature is below body temperature.
Figure 3:
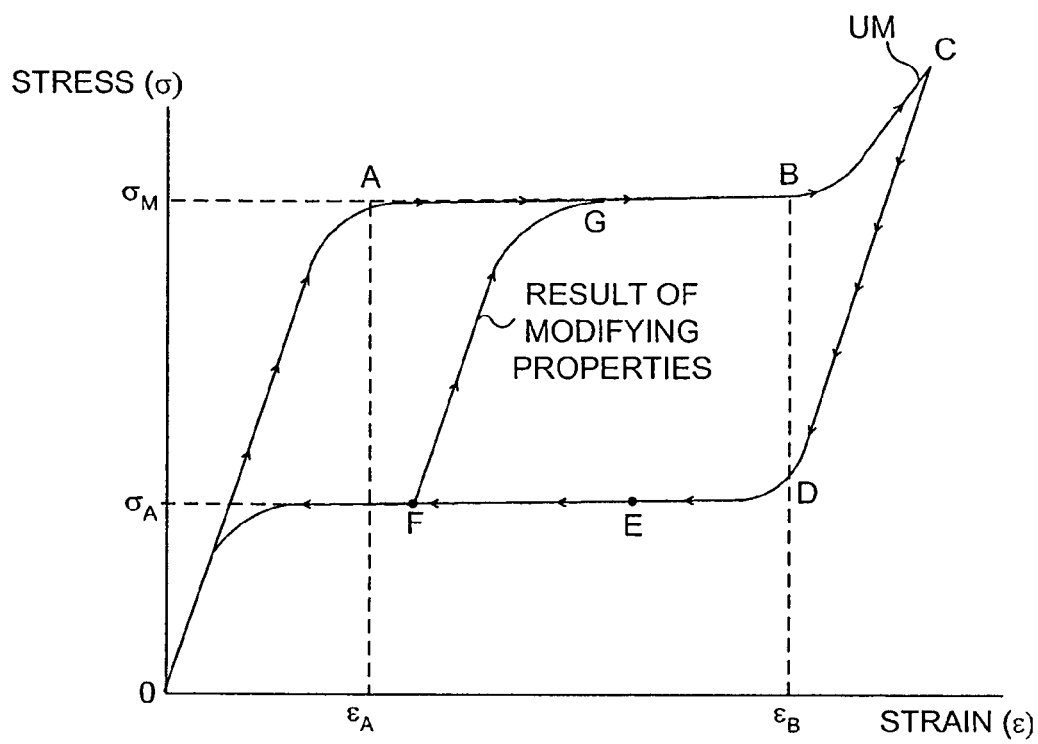
FIG. 3 illustrates the stress-strain behavior of an SMA, wherein the $A_f$ temperature of the material is below body temperature, and wherein the SMA has been transformed to a state of martensite for insertion into a delivery system, constrained as UM while delivered, then partially relaxed to a lower strain state in the coronary sinus, assisted with an external force to a further relaxed lower strain state, and made stiffer due to modulation of the SMA bias stiffness as the material is loaded with force from tissue recoil, upon removal of the external assisting force.

FIGS. 1-3 illustrate stress-strain curves for martensite-austenitic conversion of an SMA. In these Figures, the SMA is warmed to human body temperature (herein considered to be about 37° C.), which is between $M_s$ and $M_d$ for the SMA, so that the SMA is initially austenitic. The following discussion assumes that $M_s$ is equal to $M_f$ and that $A_s$ is equal to $A_f$. FIG. 1 shows the case when the $A_s$ temperature is adjusted higher than 37° C., so that any martensite formed by an applied stress is stable; while FIGS. 2 and 3 show cases where the $A_f$ temperature is adjusted below 37° C., so that austenite, at zero stress, is the only stable state, and any martensite that is formed, is unstable.

In FIG. 1, when a stress is applied to the SMA, it deforms elastically along line OA. At a critical applied stress, $\sigma_M$, the austenitic SMA begins to transform to martensite. This transformation takes place at essentially constant stress until the alloy becomes fully martensitic at point B. From that point on, as further stress is applied, the martensite yields first elastically and then plastically (only elastic deformation is shown along path BC). When the stress is released, the martensite recovers elastically to point D, at which there is zero residual stress, but a non-zero residual strain. This behavior would normally describe classic plastic deformation, except in this case, the deformation is not plastic, because the SMA can recover with the application of heat energy. Because the temperature is below this SMA's $A_s$ temperature, the deformation is not recoverable until the SMA is heated above $A_s$, resulting in a reversion of the SMA to austenite. At that point, if the sample is unrestrained, the original (programmed) shape will be essentially completely recovered; but if constrained, the SMA will recover only to the extent permitted by the constraint. However, if the material is then allowed to re-cool to the original temperature at which it was deformed, the stress produced in the sample will be constant, regardless of the strain, provided that the strain lies within the "plateau" region of the stress-strain curve, i.e., along line AB. Thus, for a strain between $\epsilon_B$ and $\epsilon_A$, the stress will be $\sigma_M$, and a known, constant force (calculable from $\sigma_M$) can be applied over a relatively wide strain range.

In FIG. 2, when a stress is applied to the SMA, it deforms elastically along line OA, then along line AB, while transforming from austenite to a martensite state. By straining the alloy further, the martensite can be deformed to point C, just as in FIG. 1. However, the stress-strain behavior upon unloading is significantly different, since the human body temperature is above the $A_s$ temperature of this alloy and the stable phase is therefore austenite. The martensite at point C is thus UM. As the stress is removed, the alloy recovers elastically from C to D and, at a critical stress, $\sigma_A$, the SMA reverts to austenite without requiring a change in temperature. Thus, reversion occurs at essentially constant stress. Finally if the stress is removed from the reverted austenite, it recovers elastically along line EO. The recoverable deformation associated with the formation and reversion of UM has been referred to as pseudoelasticity. While $\sigma_M$ may be comparatively high, e.g., more than 50 ksi, $\sigma_A$ is usually substantially lower, e.g., less than 10 ksi, thereby creating a constant-force spring with an effective working strain range of about 5% ($\epsilon_B$-$\epsilon_A$). The shape change available in the SMA, using UM, is thus self-actuated, rather than thermally actuated and controlled, permitting greater control over a device incorporating the SMA.

The key difference between the material properties of the SMAs shown in FIGS. 1 and 2 is the relationship between the SMA $A_f$ temperature and the normal body temperature of a patient. As the $A_f$ temperature is adjusted downwardly, the hysteresis region bound by the path O, A, B, C, D, E, O is raised, thus increasing internal stress at a given strain condition.

UM can be produced in an SMA having an $A_f$ temperature set below body temperature by freezing the alloy to a temperature well below its $A_f$ temperature (so that it behaves like the material shown in FIG. 1); loading the alloy to point C (and possibly then unloading the alloy to point D), as in FIG. 1; constraining the SMA in either the deformed shape while at point C or D, and then elevating the temperature of the SMA to human body temperature (which is above $A_f$), while constraining the alloy (e.g., in a catheter or a delivery device) while at points C or D, as shown in FIG. 2. In this condition, the SMA comprises UM, which will impart force on the constraining catheter, thus generating a self-actuating driving force directed to achieving a lower strain state more nearly at point E or eventually, at point O, in FIG. 2. In this case, the SMA is conditioned to a state of UM through a thermal-mechanical process. The martensite is thermally induced by cooling the SMA and then imparting stress and warming, and the deformed alloy is thus constrained in a state of UM.

FIG. 3 illustrates a stress versus strain path performed by a mitral valve reshaping device as it is loaded into a constraining catheter and/or delivery device, deployed, and then adjusted to enhance its stiffness after being deployed within the coronary sinus. By applying stress, strain, or a thermo-mechanical process as described above, the SMA can be conditioned to a state of UM at a point between point A and point C in FIG. 3. It is in this condition that the device would be positioned in the coronary sinus for use in reshaping the mitral valve annulus. Upon deployment in the coronary sinus, the reshaping device is released from its constraining delivery device, reducing stress to a point E (as shown in FIG. 3). Point E has been arbitrarily chosen as a point of reduced strain at which the device has applied force to the coronary sinus tissue and has come to a state of balanced force equilibrium with that tissue. This example illustrates how a device made from SMA material and conditioned to a state of UM, can reliably perform work on tissue in the remote location of the human coronary sinus as a self-actuated single component.

Moreover, by applying an external force to assist the mitral valve reshaping device to even further displace the surrounding coronary sinus tissue, the material stiffness of the SMA comprising the device can be adjusted and enhanced. For example, by assisting the SMA of the device to a lower strain state, such as a point F, the device can be stiffened using stored energy arising from the elasticity of the deformed tissue. As the assisting load is removed, the elastic recoil of the tissue will push the reshaping device towards a higher strain state, i.e., towards or beyond point G. The slope between F and G represents the new modulus of rigidity of this mitral valve annulus reshaping device. As the SMA in the device is allowed to relax to a lower strain state, its strain level will move onto the lower plateau curve. As the SMA is forced to a higher strain state, the strain level will move to the upper plateau curve. Therefore, by forcing the device to a higher or lower strain state, a mitral valve annulus reshaping device can be advantageously adjusted to a required stiffness to reshape the mitral valve annulus as needed to reduce mitral valve regurgitation. The ability to reversibly change between the austenitic and martensite states after the device has been deployed in the body of the patient provides greater flexibility and control of a mitral valve annulus modification using the present invention.

It will be understood that each of the embodiments discussed below can be implemented using SMA produced in accord with the preceding discussion. At least a portion of the SMA may be in an austenitic state when introduced into the body of a patient and then changed, at least partially, to a martensite state. Preferably, however, the SMA comprising the device will be constrained and introduced into the patient's body as UM. The UM state of the device can be achieved using any of the approaches discussed above.

Figure 4:
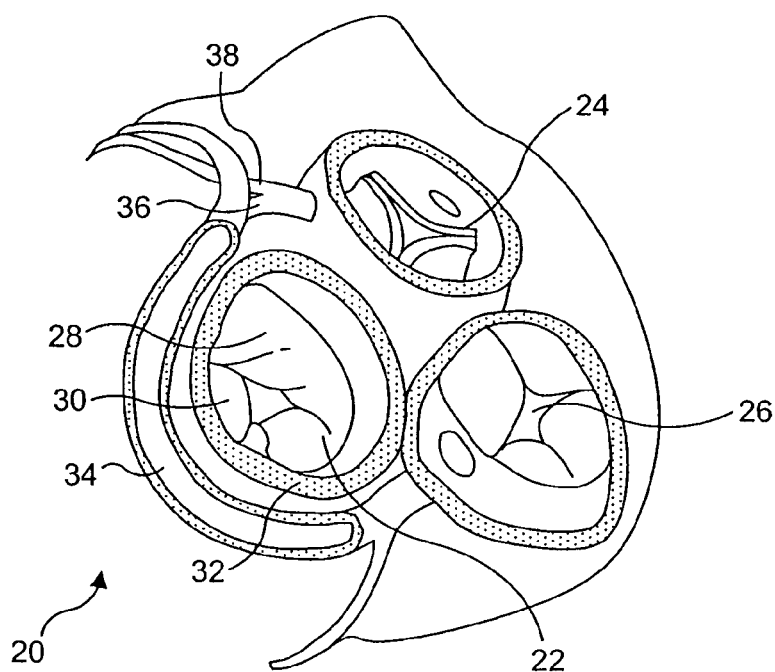
FIG. 4 is a superior view of a human heart with the atria removed to expose a plurality of valves and show the relationship between the mitral valve and the coronary sinus.

FIG. 4 illustrates a human heart 20 in which the atria has been removed to expose a mitral valve 22, an aortic valve 24, and a tricuspid valve 26. Also partially shown are a circumflex artery 36 and a coronary artery 38. Mitral valve 22, which is located between the aorta and left ventricle, includes an anterior cusp 28 and a posterior cusp 30. Surrounding the anterior cusp and posterior cusp is an annulus 32 that maintains the spacing of the cusp when a mitral valve closes during a left ventricular contraction. Coronary sinus 34 extends adjacent to annulus 32, along the atrial ventricular groove between the left atrium and left ventricle of the heart. Since coronary sinus 34 is generally coplanar with annulus 32, it is ideally disposed to facilitate modification of the shape of the annulus to correct a leakage or blood regurgitation problem with the mitral valve. The present invention takes advantage of the disposition of the coronary sinus relative to the annulus of the mitral valve by enabling insertion of a device into the patient's body, for modifying the shape of the annulus from within the coronary sinus.

Various known techniques can be employed for inserting a catheter into the coronary sinus through a venous incision to enable deployment of a mitral valve annulus device in accord with the present invention. For example, it is contemplated that the mitral valve annulus reshaping device can be constrained within a catheter in preparation for insertion within the coronary sinus, and the catheter can then be guided into the coronary sinus, using a guide wire or other appropriate means. Once thus in place, the reshaping device can either be pushed from the catheter, or the catheter can be pulled back, leaving the device in a desired position within the coronary sinus.

Figure 5:
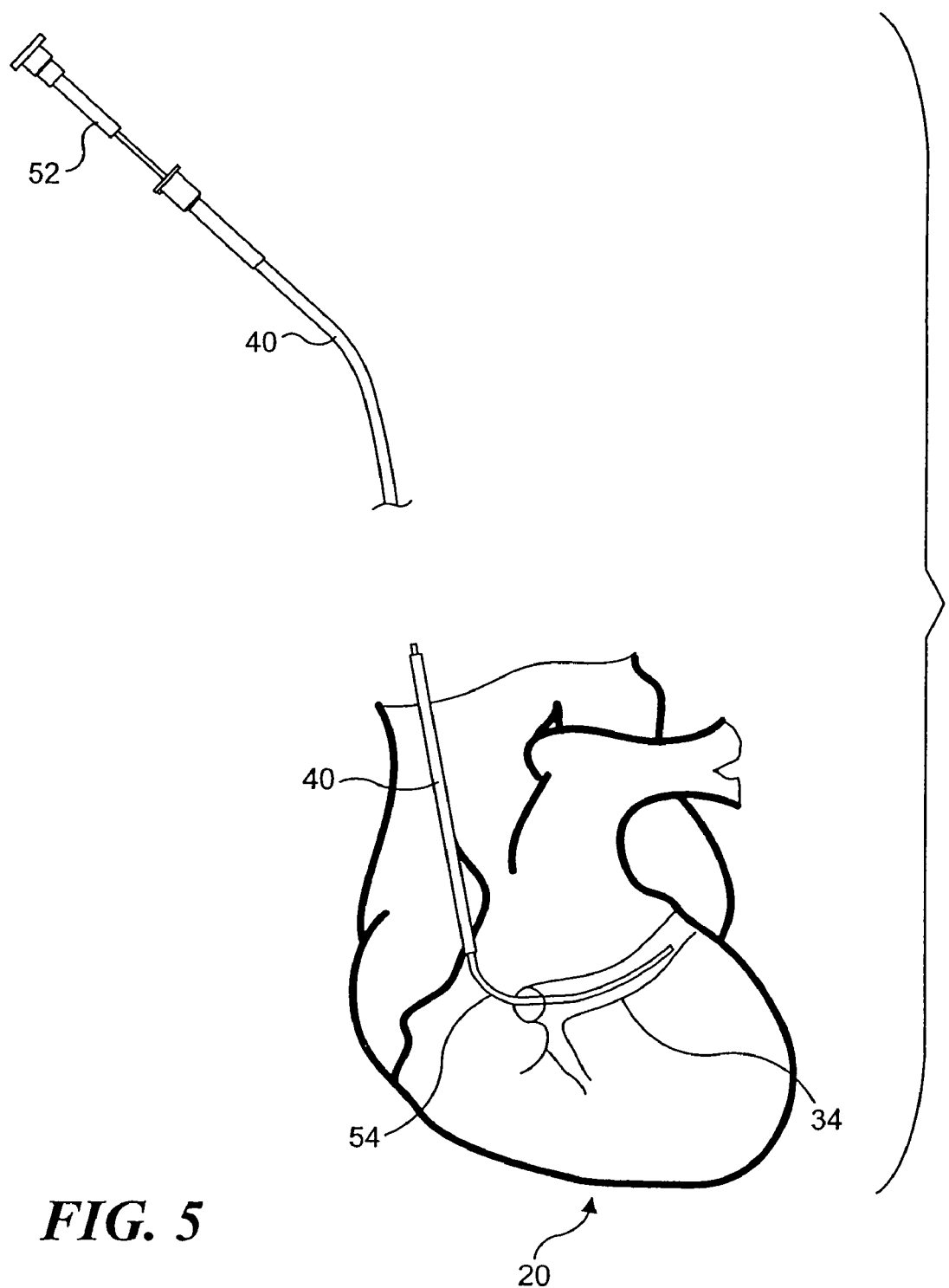
FIG. 5 is a pre-curved inner dilator and a straight guide catheter for use in introducing a mitral valve annulus reshaping device into the coronary sinus.

FIG. 5 illustrates apparatus that facilitates a preferred approach for inserting a catheter 40 into coronary sinus 34. This apparatus includes a pre-curved inner dilator 54, which can be manually shaped into a curve to match the anatomical characteristics of the patient, and which has a proximal end 52 that extends proximally of catheter 40. The pre-shaped curve in inner dilator 54 enables advancing the dilator around a relatively sharp bend, as is necessary to enter the coronary sinus. The inner dilator is used to advance the catheter through the patient's venous system and into the coronary sinus, pushing, rotating, and manipulating the dilator as required. When positioned as required for deployment of the reshaping device, the catheter will typically extend from an incision in the patient's jugular vein (not shown) and down through the vena cava. From the superior vena cava, the catheter will extend into the right atrium of the heart, and continue along the wall of the right atrium and into the coronary sinus. Once the inner dilator and catheter 40 have been advanced so that the distal end of the catheter is disposed where desired within the coronary sinus 34, the pre-curved inner dilator is withdrawn to enable insertion of the mitral valve annulus reshaping device.

Figure 6:
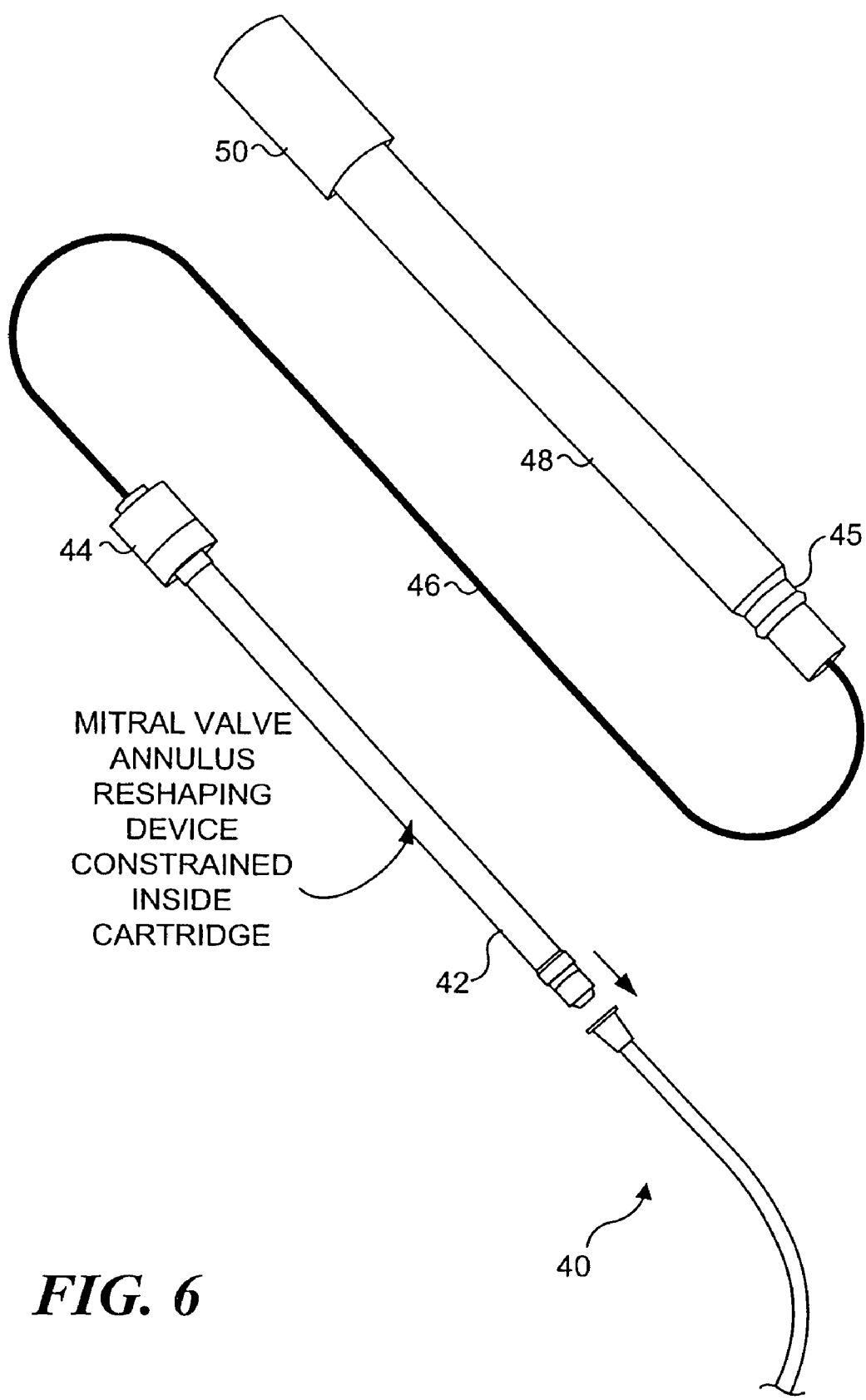
FIG. 6 is a delivery assembly for a mitral valve reshaping device constrained in a delivery cartridge adapted to couple to the catheter of FIG. 5, to enable the reshaping device to be advanced with an included pusher into and through the catheter to a delivery site in a human coronary sinus.

FIG. 6 illustrates an assembly that is preferably used for introducing a mitral valve annulus reshaping device into the coronary sinus through catheter 40. The assembly includes a cartridge 42 within which the mitral valve annulus reshaping device is constrained in a UM state. As shown in FIG. 6, cartridge 42 is coupled to the proximal end of catheter 40 to facilitate deployment of the mitral valve annulus reshaping device into the coronary sinus through the catheter. A pusher cable 46 extends from a handle 48. The distal end of handle 48 includes a snap lock 45 that engages a control knob 44, locking handle 48 onto control knob 44, while still enabling the control knob to be rotated in engagement with threads (not shown) that are formed on the exterior surface of cartridge 42. As handle 48 is brought into engagement with the control knob, pusher cable 46 advances the mitral valve annulus reshaping device from inside cartridge 42 into catheter 40 and toward the distal end of the catheter.

Once handle 48 has fully engaged and been locked onto control knob 44, the mitral valve annulus reshaping device should have been advanced to a point just within the distal end of catheter 40. Control knob 44 is then rotated in engagement with the threads on the outside of the cartridge, to advance the mitral valve annulus reshaping device from the constraint of catheter 40, into the coronary sinus of the patient. Thus, control knob 44 controls the advancement and deployment of a mitral valve annulus reshaping device within the coronary sinus. A release knob 50 is employed for uncoupling pusher cable 46 from the device after it has been fully deployed within the coronary sinus and adjusted as desired by the medical personnel using the assembly. Once the mitral valve annulus reshaping device is fully disposed within the coronary sinus, catheter 40 is withdrawn from the patient's body.

Figure 7:
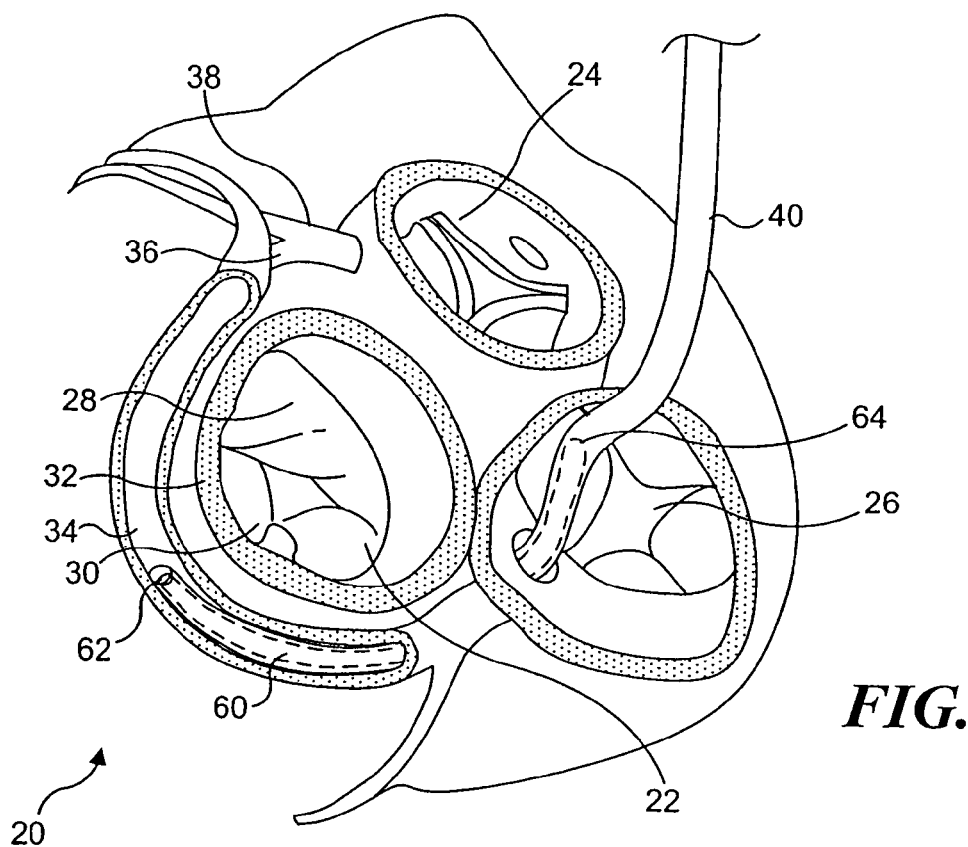
FIG. 7 shows the human heart of FIG. 4, with a mitral valve annulus reshaping device constrained within a catheter used to introduce the device into the coronary sinus.

FIG. 7 illustrates the disposition of catheter 40 within the coronary sinus while a mitral valve annulus reshaping device 60 remains inside the catheter 40, ready to be deployed within coronary sinus 34. As shown in this Figure, the mitral valve annulus reshaping device has a distal end 62 that is generally aligned with the distal end of catheter 40, while a proximal end 64 of the device is well inside catheter 40. FIG. 7 thus shows the disposition of the mitral valve annulus reshaping device prior to rotating control knob 44 to force the device from inside catheter 40 so that it is released and unconstrained within the coronary sinus.

While the mitral valve annulus reshaping device remains constrained within catheter 40, the shape memory alloy comprising the reshaping device at least partially remains as UM. The shape memory alloy comprising the device has a characteristic temperature, $A_f$, that is below or equal the normal body temperature of the patient. Accordingly, the SMA is in a super-elastic state, and the device can readily be delivered into the coronary sinus through catheter 40 while constrained in the UM state. Because the SMA of the device is superelastic, the device is readily deformed to a size that fits within the catheter and can be advanced into the coronary sinus. The interior surface of the distal portion of catheter 40 or the exterior surface of the mitral valve annulus reshaping device can be coated with a friction reducing material, such as a lubricating material or the catheter provided with a low friction lining material to facilitate deployment of the device from the distal end of the catheter.

Figure 8:
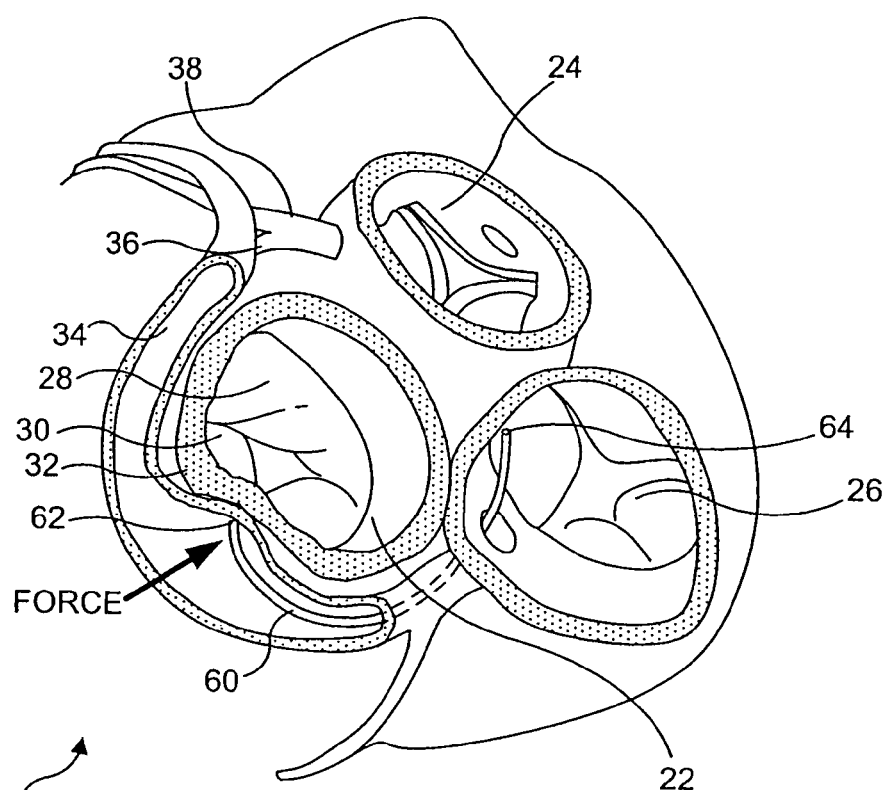
FIG. 8 shows the human heart of FIG. 4, with a mitral valve annulus reshaping device that has been deployed outside the constraint of the catheter and allowed to transform to a second state in the human coronary sinus, so that the device now has a reduced radius of curvature, producing a force that acts on the annulus of the mitral valve to modify its shape.
Figure 10:
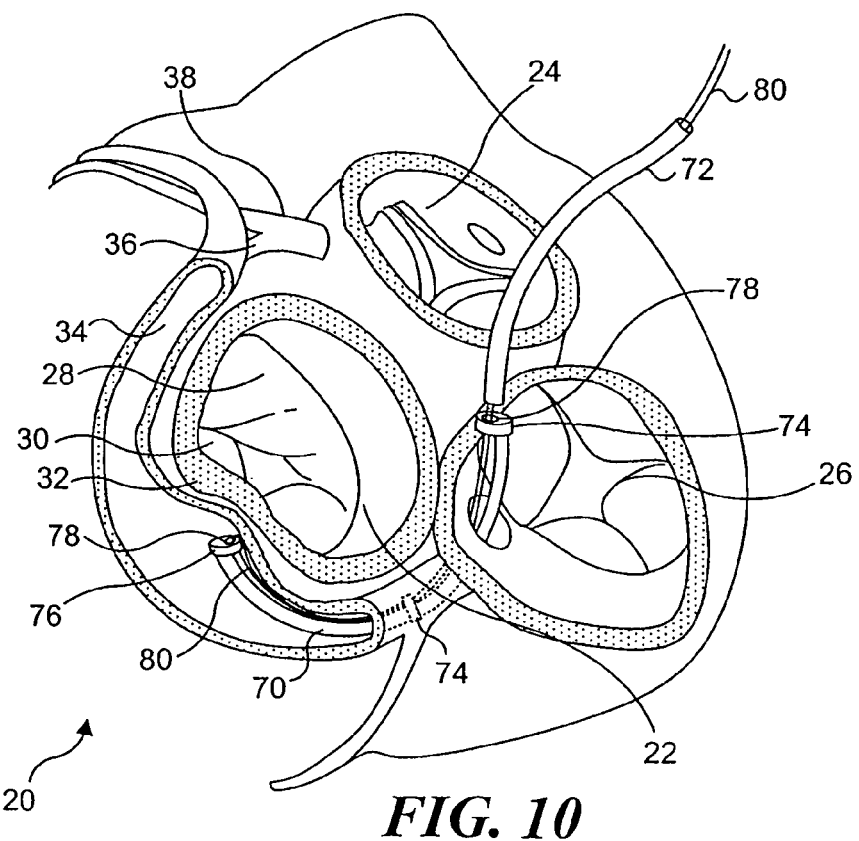
FIG. 10 shows the human heart of FIG. 4 and a side elevation view of an assembly including a pusher, a mitral valve annulus reshaping device, and a tether for modifying the radius of curvature of the device and varying the strain in the device.
Figure 11:
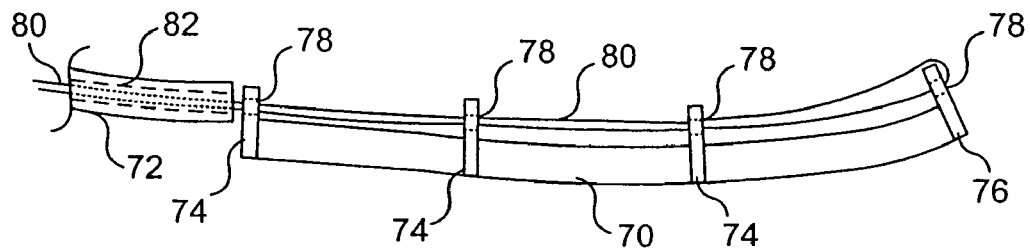
FIG. 11 is an enlarged side elevational view of the mitral valve annulus reshaping device and tether line shown in FIG. 10

The SMA comprising the mitral valve annulus reshaping device 60 at least partially converts from UM to its austenitic state once released from the constraint of the catheter as is illustrated in FIG. 8. As shown in this Figure, reshaping device 60 is fully outside of the catheter and deployed within the coronary sinus. Once the constraint of the catheter is removed, the mitral valve annulus reshaping device is enabled to change to a second, relatively lower strain state having a reduced radius of curvature, so that a distal end of the device exerts a force against the annulus of the mitral valve. This release from the constraint imposed by the catheter enables at least a partial recovery to the programmed shape of the device. The mitral valve annulus reshaping device is constrained so that its programmed shape curves with a reduced radius of curvature substantially in the plane of the mitral valve annulus, bringing the distal end of the device into contact with and exerting force upon the annulus as shown in FIG. 8. If desired, a removable tether (as shown in FIGS. 10 and 11) can, be employed to further reduce the radius of curvature of the reshaping device to reduce its internal strain condition. Once the force applied by the tether is released, an elastic recoil of the tissue on the inner surface of the coronary sinus that is in contact with the device will again load the SMA of the device, causing the strain to increase, as shown along line FG in FIG. 3. Use of the tether in this manner thereby enables adjustment of the mitral valve annulus reshaping device stiffness and the force at equilibrium with the tissue that the reshaping exerts against the interior surface of the coronary sinus at distal end 62, to reshape annulus 32.

Figure 9:
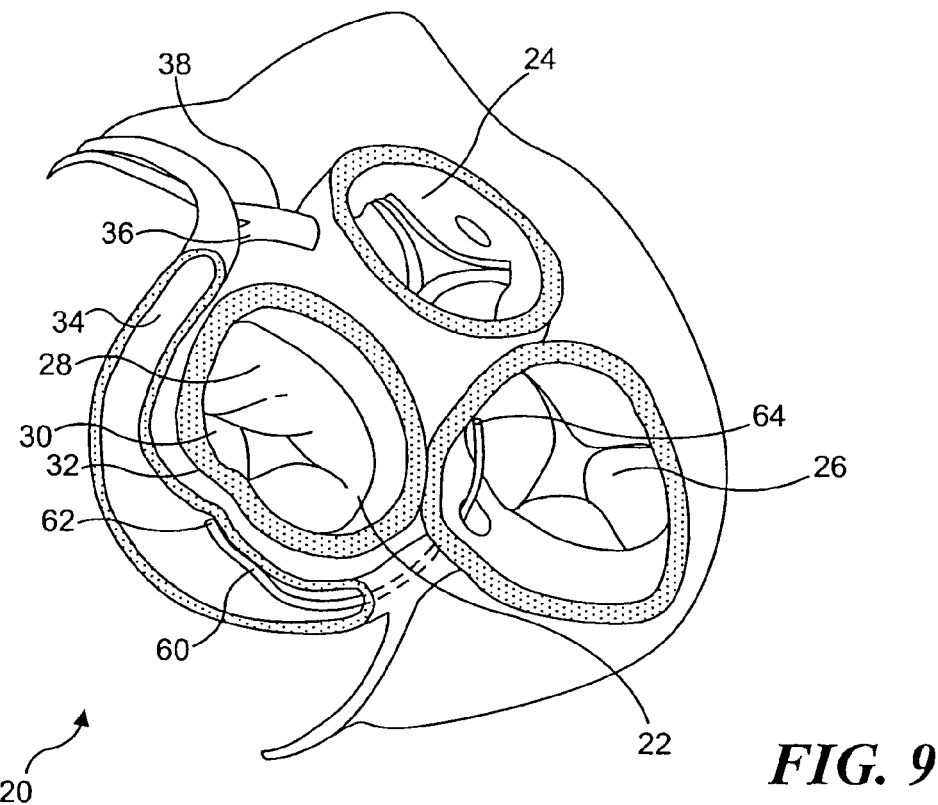
FIG. 9 shows the human heart of FIG. 4 and the mitral valve annulus reshaping device of FIG. 8, after tissue rebound has increased the strain in the SMA of the device so that it has an increased radius of curvature.

Alternatively, the SMA of the device can be modified to have less stiffness. The reduced radius of curvature of the annulus in FIG. 8 is in contrast to the increased radius of curvature of the annulus as shown in FIG. 9. In this case, the programmed shape of mitral valve annulus reshaping device 60 has been modified using a straightening rod (not shown) that is inserted through the catheter, before the catheter is removed from the venous system of the patient. The straightening rod can be temporarily advanced into the coronary sinus, to act upon the mitral valve annulus reshaping device so as to increase the radius of curvature of the reshaping device and thereby reduce internally stored strain. In this manner, the straining rod is used to adjust the mitral valve annulus reshaping device stiffness and reduce the normal force applied by the reshaping device against the tissue of the coronary sinus adjacent to the mitral valve annulus. By monitoring physiological parameters such as blood pressure, fluoroscopic images, ultrasound flow patterns through the heart, and an electrocardiogram of the patient, medical personnel can determine the effect of reshaping the annulus of the mitral valve and modify the extent of the reshaping as necessary to achieve a desired improvement in the functioning of the mitral valve. Clearly, a physician will desire to provide an optimal correction of a defect in the mitral valve, and the present invention provides the means to vary the degree to which the annulus is reshaped and thereby control the changes to the mitral valve operation as desired.

FIGS. 10 and 11 illustrate a mitral valve annulus reshaping device 70 that can readily be modified once it has been disposed within the coronary sinus of a patient. In this embodiment, device 70 is pushed from catheter 40 (not shown in this Figure) using a pusher 72, which can remain in place after catheter 40 has been partially withdrawn. Coupled to device 70 is a tether 80, which extends through a lumen 82 in pusher 72 and through a plurality of bores 78 formed within guides 74 that are disposed at spaced apart locations along the longitudinal access of device 70. An end terminal 76 is disposed at the distal end of mitral valve annulus reshaping device 70, and tether 80 also extends through bores 78 within end terminal 76, and loops back through bores 78 in each of guides 74, extending out through lumen 82 in pusher 72 to the proximal end of the pusher, which is disposed outside the body of the patient (not shown). As illustrated in FIG. 10, when unconstrained by catheter 40, reshaping device 70 at least partially converts from UM to its austenitic state in which it attempts to assume its programmed curved shape. Since the characteristic temperature $A_f$ is below the normal body temperature of the patient, the austenitic state can be achieved, at least partially, while mitral valve annulus reshaping device 70 is within the body of the patient. As is most clearly illustrated in FIG. 11, tether 80 can be pulled while holding pusher catheter 82 against the proximal end of device 70, to assist the device in applying force against the adjacent tissue of the coronary sinus after the reshaping device has been deployed within the coronary sinus. Using the tether end pusher catheter 72 in this manner, it is possible to reduce the reshaping device radius of curvature and thereby reduce its internally stored strain condition, until the tether is released, which then increases the loading and strain on the device. As discussed above, the effect of this increase in the strain experienced by the reshaping device is to modify the stiffness of the device. Accordingly, it should be apparent that the tension applied by tether 80 is usable to adjust the stiffness of the mitral valve annulus reshaping device and thereby vary the force that it applies against tissue adjacent to the mitral valve annulus within the coronary sinus. Once the desired stiffness and force have been achieved by mitral valve annulus reshaping device 70, one end of tether 80 can be released, and the other end pulled to withdraw the tether through bores 78. The pusher catheter 72 can then be withdrawn from the venous system of the patient, leaving device 70 in place.

Figure 12:
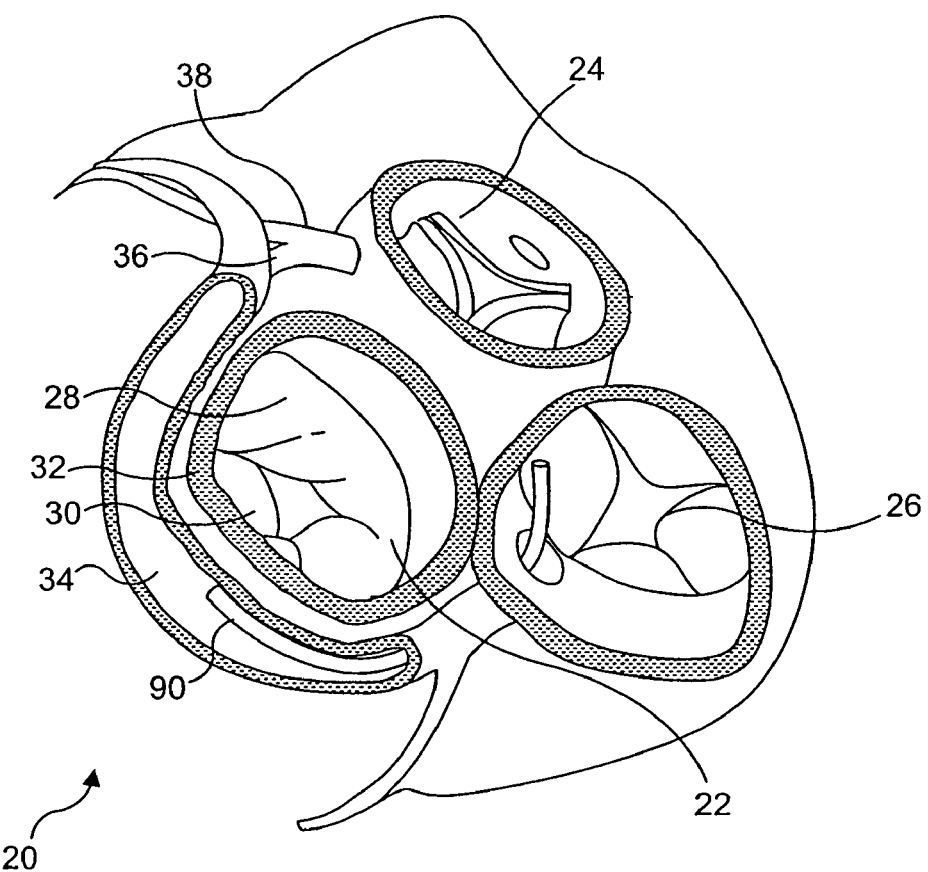
FIG. 12 shows the human heart of FIG. 4, with a mitral valve annulus reshaping device that has been allowed to transform to a second state, in the human coronary sinus, where the second state increases the radius of curvature of the mitral valve annulus.

As shown in FIG. 12, the second state and programmed shape of the SMA comprising a mitral valve reshaping device 90 and its placement in the coronary sinus can be chosen to cause an increase in the radius of curvature of the annulus when the constraint of the catheter is removed, in contrast to the decrease in radius of curvature of the annulus caused by the embodiment of FIGS. 8 and 9. For some patients, an increase in the radius of curvature of the annulus may be preferred to a decrease in the radius of curvature to correct problems with leakage through the mitral valve.

Figure 13:
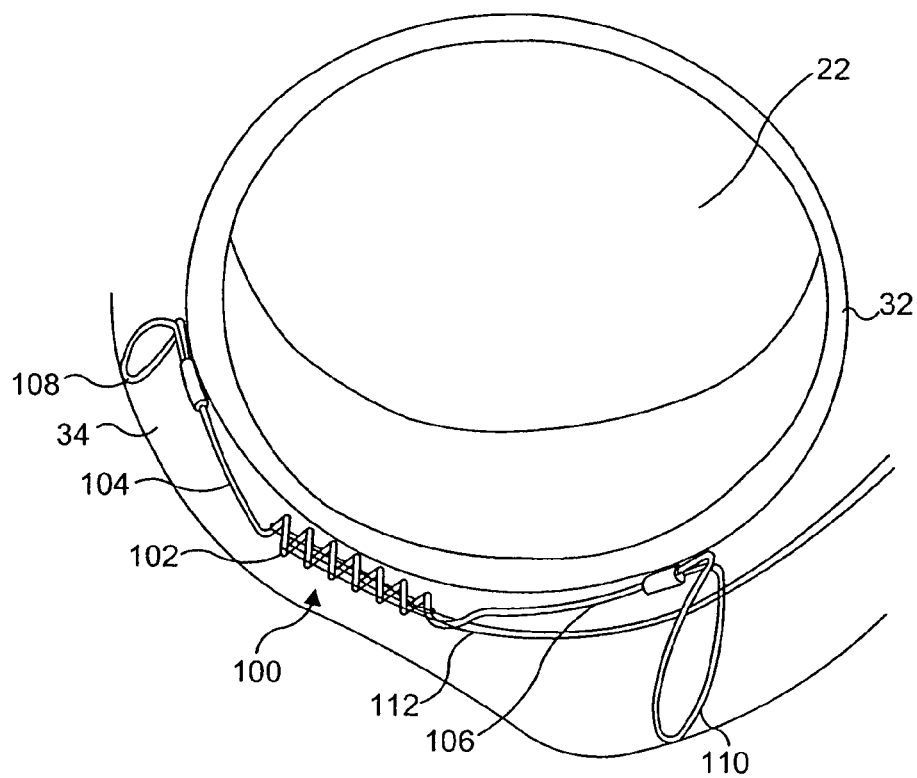
FIG. 13 shows a mitral valve annulus reshaping device comprising dedicated anchor elements that are self-actuated from a state of unstable martensite to a second state with an SMA spring connector and bias stiffness adjusting tether in a human coronary sinus.
Figure 14:
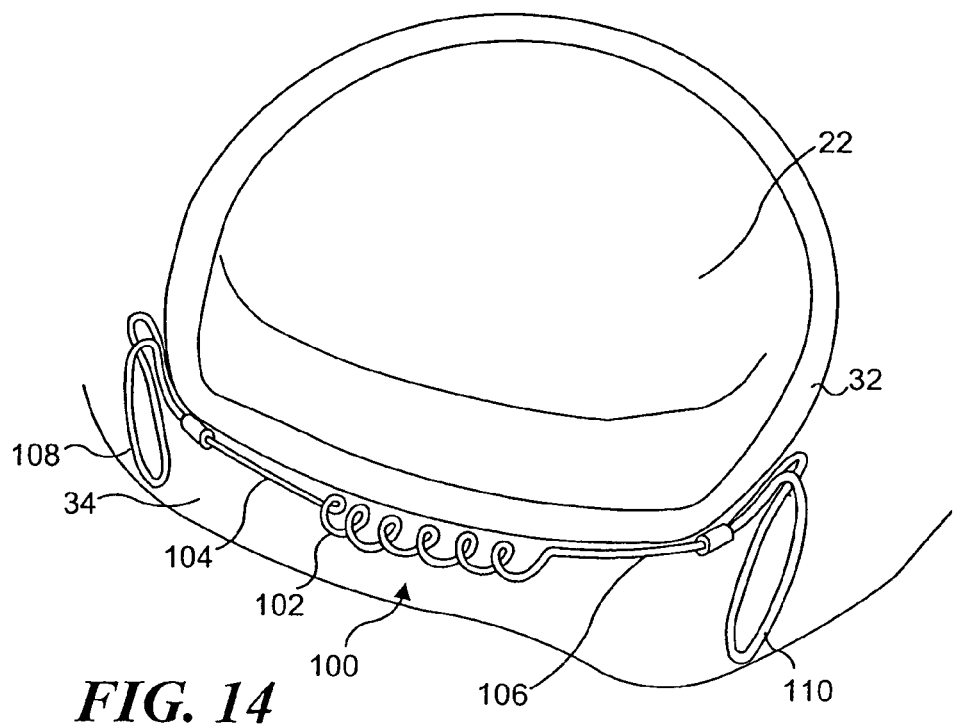
FIG. 14 is the mitral valve annulus reshaping device of FIG. 13, wherein the SMA spring connector has been adjusted to increase the spring element stiffness and thus straighten the coronary sinus to reshape the mitral valve annulus.

FIGS. 13 and 14 illustrate a mitral valve annulus reshaping device 100 that includes helical coil spring 102 disposed between straight wire sections 104 and 106. The helical coil spring is preferably formed of SMA. A distal anchor 108 is also formed from SMA and is initially deployed and permitted to at least partially change from UM to its austenitic state as the device is initially pushed (and/or pulled) from catheter 40 (not shown in this view). For this embodiment, catheter 40 is initially positioned within coronary sinus 34 at a location such that as mitral valve annulus reshaping device 100 is forced from the distal end of the catheter and distal anchor 108 is allowed freedom from the constraint of the catheter, the distal anchor 108 will change from its UM state toward its austenitic state in which it has a loop shape with a relatively larger radial extent than when constrained inside the catheter.

The released loop expands radially outward and engages the interior surface of the coronary sinus, over a distributed area. Thereafter, the catheter is withdrawn further, beyond helical coil spring 102, finally enabling a proximal anchor 110 to be freed from the constraint of the catheter. The proximal anchor also at least partially changes from the UM state toward the austenitic state, enabling the expanding loop shape of the proximal anchor 110 to anchor device 100 at its desired disposition within the coronary sinus.

Prior to deploying and releasing the constraint on proximal anchor 110, the user will apply tension to a tether line 112. The tether line forms a double loop around and through the distal and proximal ends of helical coil spring 102. The tensile load resulting from the application of a tensile load on the tether line will cause straight wire sections 104 and 106 and helical coil spring 102 to form UM. The proximally applied tension in the tether line pulls the distal anchor, straight wire section 104, and tissue distal to the helical coil spring in the proximal direction. The helical coil spring will thus be assisted to relax to its tightly wound programmed shape, which is therefore at a lower strain state. Upon release of the tension produced by the tether line, elastic tissue recoil and internal heart pressure will load the previously relaxed helical coil spring and transform the spring stiffness to a higher level. Thus, by applying tensile load to the tether line, the reshaping device spring stiffness and length are adjusted to an appropriate level required to reshape adjacent tissue and the mitral valve annulus, and thereby reduce mitral valve regurgitation. Also, the tension applied to tether line 112 determines the force applied against the adjacent tissue to modify the shape annulus 32, before the final disposition of proximal anchor 110 is determined.

In FIG. 14, spring stiffness has been increased in the helical coil 102 causing the mitral valve annulus reshaping device to straighten the adjacent tissue and annulus 32. FIG. 14 also illustrates the reshaping device after tether line 112 has been removed, which is accomplished by releasing one end of the tether line and pulling the tether line from the loops around the coils of the helical coil spring.

Yet another embodiment of the present invention is shown in FIG. 15 wherein a mitral valve annulus reshaping device 120 is illustrated. This device also includes a helical coil 122, which is disposed between straight sections 124 and 126 a tether 132 for adjusting the stiffness of the spring and the relative force applied by the device against the adjacent tissue and mitral valve annulus. However, mitral valve annulus reshaping device 120 includes a distal stent 128 and a proximal stent 130 that are also preferably formed of SMA. Distal stent 128 is allowed to expand as it converts from UM toward its austenitic state once the constraint of the catheter is removed. Thus, once again it is important that the distal end of catheter 40 be disposed within coronary sinus at about the location where distal stent 128 is to be disposed as it is allowed to expand to its programmed shape. By applying appropriate stress on tether line 132, the user can modify the tension distal of helical coil 122 and thereby achieve a desired modification of annulus 32. In addition, the user can modify the strain and stress by varying the tension in tether line 132 to change the force applied to the adjacent tissue by device 120, using the tether line to change the stress applied to the helical coils of the SMA comprising the device. Accordingly, mitral valve annulus reshaping device 120 is very similar to the embodiment shown in FIGS. 13 and 14. As an alternative, it is contemplated that one or both of the distal and proximal stents of this embodiment might be made of a non-SMA metal, or of an SMA metal whose $A_f$ is above normal body temperature, and expanded radially into contact with the interior surface of the coronary sinus using a conventional catheter inflatable balloon coupled to an external source of a pressurized fluid.

FIGS. 16-18 illustrate another embodiment of the mitral valve annulus reshaping device that includes an SMA metal wire or arched leaf spring 140 with a programmed shape having a relatively small radius of curvature, R. At each end of arched leaf spring 140 are disposed loops 142 and 144, also preferably formed of super-elastic SMA so that they elastically expand radially outward when released from a catheter or other restraint that is used to insert the mitral valve annulus reshaping device intravenously into coronary sinus 34 of a patient. When the device is released from the constraint of the catheter or other device that is used to introduce the device into the coronary sinus, the SMA metal comprising the device it will change from its UM state toward its austenitic state. Thus, when loop 142 is released from the catheter, the expansion of loop 142, as the SMA material comprising it returns to its programmed shape, will bring the loop into contact with the inner surface of coronary sinus 34, so as to anchor the distal end of the mitral valve annulus reshaping device at a desired location and orientation within the coronary sinus.

A tether 146 passes through loop 144, and both ends of the tether extend outside the patient's body through the venous system within the catheter (not shown), enabling medical personnel to apply tension to the tether after the distal end of arched leaf spring 140 has been deployed within the coronary sinus and anchored by loop 142. Using tether 146, it is possible to applying loading tension to arched leaf spring 140, thereby adjusting the stiffness of the arched leaf spring and the relative force applied by the device against the adjacent tissue and mitral valve annulus, prior to releasing loop 144 from the constraint of the catheter. The applied tension tends to straighten arched leaf spring 140, so that it has a greater radius of curvature, R', as shown in FIG. 17, when fully deployed within coronary sinus 34. The tension applied by tether 146 is then partially unloaded. Tether 146 can be employed to make further adjustments to the device by loading and unloading the tension applied, reversibly tuning the device from UM to austenite and back. As shown in FIG. 18, the arched loop has been tuned in this manner to have an even greater radius of curvature, R", relative to its initial programmed curved radius of curvature, R, which is shown in FIG. 16.

Each of the embodiments disclosed above illustrates how SMA and its super-elasticity can be applied in modifying the shape of the annulus and thereby correcting defects in a mitral valve within the body of a patient. The characteristics of the SMA comprising each of these embodiments, as illustrated in FIG. 3, is employed to good effect, since it permits the user to modify the stiffness of the SMA comprising the device and the force applied to the adjacent tissue by the SMA even after the mitral valve annulus reshaping device has been deployed in the coronary sinus. The SMA can be reversibly changed between the martensite and austenitic states while within the body of the patient, as necessary to achieve a desired modification of the annulus and corresponding improvement in the functioning of the mitral valve. By monitoring the physiological condition of the patient, it is thus possible for medical personnel to achieve a near optimum correction of a defect in a mitral valve with the present invention, without the risks of open heart surgery and with none of the problems associated with mitral valve replacement.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A method of reshaping a mitral valve annulus comprising:
compressing a mitral valve annuloplasty device into a catheter, the mitral valve annuloplasty device comprising a first anchor and a second anchor and a connector between said anchors, the connector comprising a spring;
maintaining a tensile force in the spring;
placing the catheter in a lumen adjacent to the mitral valve annulus;
removing the catheter from at least part of the device and engaging the first anchor with a wall of the lumen;
after the removing step and the engaging step, releasing the tensile force from the spring, wherein releasing the tensile force from the spring causes the connector to shorten.

2. The method of claim 1 wherein maintaining a tensile force in the spring comprises maintaining an axially directed tensile force.

3. The method of claim 2 wherein maintaining an axially directed tensile force comprises maintaining a proximally directed tensile force.

4. The method of claim 1 wherein releasing the tensile force from the spring further causes the connector to straighten.

5. A method of reshaping a mitral valve annulus comprising:
providing a mitral valve annuloplasty device within a catheter in a delivery configuration, the mitral valve annuloplasty device comprising a first anchor and a second anchor and a connector between said anchors, the connector comprising a spring;
maintaining the spring in an elongated configuration;
placing the catheter in a lumen adjacent to the mitral valve annulus;
removing the catheter from at least part of the device and engaging the first anchor and second anchor with a wall of the lumen such that the device assumes a first configuration with a first radius of curvature;
after the removing step and the engaging step, releasing the spring from the elongated configuration to allow it to assume a second configuration shorter than the elongated configuration.

6. The method of claim 5 wherein maintaining the spring in an elongated configuration comprises maintaining a force in the spring.

7. The method of claim 6 wherein maintaining force in the spring comprises maintaining an axially directed force.

8. The method of claim 5 wherein releasing the spring from the elongated configuration causes the connector to straighten.

9. A mitral valve annuloplasty device for reshaping a mitral valve annulus comprising:
a first expandable anchor and a second expandable anchor and a connector between said anchors, the connector comprising a spring;
wherein the device is adapted to be delivered in a catheter to a lumen adjacent to the mitral valve annulus,
wherein the device is configured to assume a first configuration with a first radius of curvature in which the first and second anchors are expanded when released from the catheter to engage the walls of the lumen,
wherein the device is configured to assume a second configuration with a second radius of curvature when the spring is released from a tensile force, and
wherein the connector is adapted to shorten when it is released from the tensile force.

10. The device of claim 9 wherein the coil spring is further adapted to straighten when it is released from the tensile force.

11. A method of reshaping a mitral valve annulus comprising:
providing a mitral valve annuloplasty device within a catheter in a delivery configuration, the mitral valve annuloplasty device comprising a first expandable anchor and a second expandable anchor and a connector between the anchors, the connector comprising a spring;
placing the catheter in a lumen adjacent to the mitral valve annulus;
maintaining the spring in an elongated configuration;
expanding the first anchor and the second anchor to engage a wall of the lumen such that the device assumes a first configuration;
releasing the spring from the elongated configuration to allow it to assume a second configuration shorter than the elongated configuration.

12. The method of claim 11 wherein maintaining the spring in an elongated configuration comprises maintaining a force in the spring.

13. The method of claim 11 wherein maintaining a force in the spring comprises applying a force on the spring by a tensioning element at a location between the proximal and distal anchors.

14. The method of claim 11 wherein releasing the spring from the elongated configuration causes the connector to straighten.

* * * * *